(12) United States Patent
Albisetti (10) Patent No.: US 10,413,036 B2
(45) Date of Patent: Sep. 17, 2019

(54) AEROSOL CONTAINING AN EMULSION DEODORANT, EQUIPPED WITH A HOLLOW DISPENSING HEAD

(71) Applicant: L'OREAL, Paris (FR)

(72) Inventor: Nicolas Albisetti, Saint Gratien (FR)

(73) Assignee: L'OREAL, Paris (FR)

( * ) Notice: Subject to any disclaimer, the term of this patent is extended or adjusted under 35 U.S.C. 154(b) by 196 days.

(21) Appl. No.: 14/902,587

(22) PCT Filed: Jul. 4, 2014

(86) PCT No.: PCT/FR2014/051723
§ 371 (c)(1),
(2) Date: Jan. 3, 2016

(87) PCT Pub. No.: WO2015/001272
PCT Pub. Date: Jan. 8, 2015

(65) Prior Publication Data
US 2016/0166042 A1    Jun. 16, 2016

(30) Foreign Application Priority Data
Jul. 4, 2013 (FR) .................................. 13 56572

(51) Int. Cl.
*A45D 34/00* (2006.01)
*A61Q 15/00* (2006.01)
(Continued)

(52) U.S. Cl.
CPC ............. *A45D 34/00* (2013.01); *A45D 34/04* (2013.01); *A61K 8/06* (2013.01); *A61K 8/062* (2013.01);
(Continued)

(58) Field of Classification Search
CPC ......... B05B 1/06; B05B 1/3447; B05B 7/063; B05B 7/065; B05B 1/207; B05B 7/061;
(Continued)

(56) References Cited

U.S. PATENT DOCUMENTS 3,061,199 A    10/1962 Billeter
3,462,085 A    8/1969 Nugarus
(Continued)

FOREIGN PATENT DOCUMENTS

CN    1169111 A    12/1997
CN    1268883 A    10/2000
(Continued)

OTHER PUBLICATIONS

International Search Report for PCT/FR2014/051722, dated Sep. 11, 2014.
(Continued)

*Primary Examiner* — Arthur O. Hall
*Assistant Examiner* — Juan C Barrera
(74) *Attorney, Agent, or Firm* — The Marbury Law Group, PLLC (57) ABSTRACT

The subject of the invention is a device for dispensing a cosmetic composition, comprising a dispensing head (1) intended to be fitted on a container containing said cosmetic composition to be dispensed,
(i) the dispensing head comprising:
a body (3) that is open at its two opposite axial ends,
an engaging part (10) that is open at its two opposite axial ends and at least partially defines at least one dispensing orifice (12), the individual cross section of the dispensing orifice being between 0.03 mm$^2$ and 0.5 mm$^2$, and
(ii) the cosmetic composition comprising, in a cosmetically acceptable medium,
(Continued)

at least one emulsion chosen from a water-in-oil emulsion and an oil-in-water emulsion, at least one cosmetic active agent, in particular at least one deodorant active agent and/or antiperspirant active agent.

12 Claims, 6 Drawing Sheets

(51) Int. Cl.
| | |
|---|---|
| B05B 1/06 | (2006.01) |
| B65D 83/20 | (2006.01) |
| B65D 83/30 | (2006.01) |
| A61K 8/06 | (2006.01) |
| A45D 34/04 | (2006.01) |
| B65D 83/28 | (2006.01) |
| B65D 83/14 | (2006.01) |
| B05B 7/04 | (2006.01) |

(52) U.S. Cl.
CPC .............. *A61K 8/064* (2013.01); *A61Q 15/00* (2013.01); *B05B 1/06* (2013.01); *B65D 83/205* (2013.01); *B65D 83/28* (2013.01); *B65D 83/30* (2013.01); *B65D 83/752* (2013.01); *A45D 2200/057* (2013.01); *A61K 2800/87* (2013.01); *B05B 7/0425* (2013.01)

(58) Field of Classification Search
CPC ......... B05B 1/18; B05B 7/067; B05B 7/0425; B65D 83/20; B65D 83/30; B65D 83/28; B65D 83/205; B65D 83/752; A45D 34/00; A45D 34/04; A45D 2200/057; A61K 8/06; A61K 8/062; A61K 8/064; A61K 2800/87; A61Q 15/00
USPC ................ 239/337, 310, 341, 315, 550, 302
See application file for complete search history.

(56) References Cited

U.S. PATENT DOCUMENTS

| | | | |
|---|---|---|---|
| 3,618,857 A | 11/1971 | Rautenbach et al. | |
| 3,724,976 A | 4/1973 | Rode | |
| 3,762,649 A | 10/1973 | Dalhaus | |
| 3,767,125 A * | 10/1973 | Gehres | B05B 1/14 239/552 |
| 3,785,560 A | 1/1974 | Hruby, Jr. | |
| 3,792,068 A | 2/1974 | Luedders et al. | |
| 3,972,273 A | 8/1976 | Carlson et al. | |
| 4,195,780 A | 4/1980 | Inglis | |
| 4,592,509 A * | 6/1986 | Moss | B05B 1/005 239/424 |
| 4,606,777 A | 8/1986 | Brow | |
| 4,836,702 A | 6/1989 | Allen | |
| 4,991,314 A | 2/1991 | Allen | |
| 5,215,260 A * | 6/1993 | Robbins | B05B 1/06 239/590.5 |
| 5,273,191 A * | 12/1993 | Meshberg | B05B 11/0018 222/105 |
| 5,297,739 A * | 3/1994 | Allen | A46B 17/06 239/530 |
| 5,632,421 A | 5/1997 | Colombo | |
| 5,730,332 A * | 3/1998 | Zimmerhackel | B05B 7/0068 222/148 |
| 5,798,111 A | 8/1998 | Kanga et al. | |
| 6,257,503 B1 | 7/2001 | Baudin | |
| 6,403,070 B1 | 6/2002 | Pataut et al. | |
| 6,463,943 B1 | 10/2002 | Monroe | |
| 6,632,421 B2 | 10/2003 | Ascione et al. | |
| 6,916,465 B2 * | 7/2005 | Panzer | A61K 8/0241 424/400 |
| 6,971,557 B2 * | 12/2005 | Mather | B65D 83/206 222/182 |
| 7,427,039 B1 | 9/2008 | Jou | |
| 7,500,621 B2 * | 3/2009 | Tryon | B65D 83/205 222/402.1 |
| 8,794,543 B2 | 8/2014 | Leber | |
| 8,967,499 B2 | 3/2015 | Lee | |
| 9,326,484 B2 | 5/2016 | Allen | |
| 9,700,902 B2 | 7/2017 | Albisetti | |
| 2002/0127193 A1 | 9/2002 | Ascione et al. | |
| 2005/0063928 A1 | 3/2005 | Witham et al. | |
| 2005/0084464 A1 | 4/2005 | McGrath et al. | |
| 2005/0084474 A1 | 4/2005 | Wu et al. | |
| 2008/0001006 A1 * | 1/2008 | Monterrosa | B65D 83/30 239/288.5 |
| 2009/0060710 A1 * | 3/2009 | Gammack | F04D 25/06 415/90 |
| 2010/0150699 A1 * | 6/2010 | Nicolas | F04D 25/08 415/90 |
| 2010/0225012 A1 * | 9/2010 | Fitton | F24F 1/01 261/116 |
| 2010/0260698 A1 | 10/2010 | Galante et al. | |
| 2010/0276519 A1 | 11/2010 | Lee | |
| 2012/0014897 A1 | 1/2012 | Banowski et al. | |
| 2012/0020906 A1 | 1/2012 | Banowski et al. | |
| 2012/0234947 A1 | 9/2012 | Takahashi | |
| 2013/0221218 A1 | 8/2013 | Lee et al. | |

FOREIGN PATENT DOCUMENTS

| | | |
|---|---|---|
| CN | 1933912 A | 3/2007 |
| CN | 102059181 A | 5/2011 |
| DE | 29622069 U1 | 3/1997 |
| EP | 1052023 A1 | 11/2000 |
| EP | 1658863 A1 | 5/2006 |
| JP | S61-130523 A | 6/1986 |
| JP | 02-295912 A | 12/1990 |
| JP | 2001-232249 A | 8/2001 |
| JP | 2013-175449 A | 9/2013 |
| WO | 2005/095000 A2 | 10/2005 |
| WO | 2011/065413 A1 | 6/2011 |
| WO | 2012/075899 A1 | 6/2012 |
| WO | 2015/001271 A1 | 1/2015 |
| WO | 2015/001273 A1 | 1/2015 |

OTHER PUBLICATIONS

International Search Report for PCT/FR2014/051723, dated Sep. 25, 2014.
International Search Report for PCT/FR2014/051724, dated Dec. 18, 2014.
English language abstract for JP 02-295912A (Dec. 6, 1990).
Non-Final Office Action for copending U.S. Appl. No. 14/902,585, dated Feb. 8, 2017.
Chinese First Office Action for counterpart CN Application No. 201480037888.4, dated Dec. 2, 2016 (with machine translation).
Machine Translation of Chinese First Office Action for counterpart CN Application No. 201480037889.9, dated Dec. 1, 2016.
Non-Final Office Action for copending U.S. Appl. No. 14/902,588, dated May 16, 2017.
Final Office Action for copending U.S. Appl. No. 14/902,585, dated Nov. 24, 2017.
Final Office Action for copending U.S. Appl. No. 14/902,588 dated Feb. 7, 2018.
Non-Final Office Action for copending U.S. Appl. No. 14/902,585, dated Jun. 1, 2018.
Non-Final Office Action for copending U.S. Appl. No. 14/902,588, dated Jun. 29, 2018.
Notification of Reasons for Refusal for counterpart JP Application No. 2016-552845, dated Aug. 6, 2018 (translated).
Notification of Reasons for Refusal for counterpart JP Application No. 2016-522846, dated Aug. 6, 2018 (translated).
Final Office Action for copending U.S. Appl. No. 14/902,585, dated Jan. 7, 2019.

(56) References Cited

OTHER PUBLICATIONS

Final Office Action for copending U.S. Appl. No. 14/902,588, dated Jan. 7, 2019.

\* cited by examiner

AEROSOL CONTAINING AN EMULSION DEODORANT, EQUIPPED WITH A HOLLOW DISPENSING HEAD

CROSS REFERENCE TO RELATED APPLICATION

This is a national stage application of PCT/FR2014/051723, filed internationally on Jul. 4, 2014, which claims priority to French Application No. 1356572, which was filed on Jul. 4, 2013.

The present invention relates to dispensing heads used for dispensing a product contained in a container, in particular for spraying it.

The invention relates more particularly, but not exclusively, to spray heads intended to be fitted on pressurized containers that contain cosmetic deodorant or antiperspirant products.

Numerous spray heads have been proposed, having one or more dispensing orifice(s). Numerous parameters should be taken into consideration when designing a spray head.

First of all, the spray generated should have the granulometry suitable for the application. In this respect, the size of the droplets should not be too small or too large.

Furthermore, the spray generated should be delivered at the flow rate required and the spray head should not subject the flow of product to an excessive pressure drop.

The form of the spray should likewise correspond to the intended application and thus make it possible, as the case may be, to cover a more or less extensive area.

Finally, the spray head should be aesthetically pleasing to the consumer, and its manufacture should be compatible with the requirements of large-scale production.

Application EP 1 052 023 A1 discloses a spray head comprising a dispensing orifice defined between a closure member having a frustoconical part and the body of the head. The closure member is opened by deformation of the frustoconical part, under the pressure of the product during dispensing. A conical and hollow spray is formed at least in the vicinity of the head.

Application WO 2011/065413 discloses various arrangements of spray heads in which a spray orifice is defined between a peripheral part and a central part which are connected together by bridges of material.

The invention aims to propose a novel dispensing head which is very particularly suitable for spraying a cosmetic deodorant or antiperspirant product.

The invention also aims to propose a novel spray head which produces a totally original visual effect compared with that which exists currently.

The invention also aims to propose a spray head that gives, on application, a sensation different from the sensations felt with the current devices.

Moreover, the spraying should be effective for the intended application.

In particular, in the field of deodorants or antiperspirants, spray heads with which it is possible to precisely reach a given target are desired.

There is a need to increase the speed of application of a product by spraying without, however, increasing the risks of blockage related to the drying of the sprayed product.

The invention thus aims to further improve the known devices while making possible the use of manufacturing techniques having a cost compatible with large-scale distribution.

A subject of the invention, according to a first of its aspects, is a device for dispensing a cosmetic composition, comprising a dispensing head intended to be fitted on a container containing said cosmetic composition to be dispensed, (i) the dispensing head comprising:
a body that is open at its two opposite axial ends,
an engaging part that is open at its two opposite axial ends and at least partially defines at least one dispensing orifice, the individual cross section of the dispensing orifice being between 0.01 mm$^2$ and 0.5 mm$^2$, and
(ii) the cosmetic composition comprising, in a cosmetically acceptable medium,
at least one emulsion chosen from a water-in-oil emulsion and an oil-in-water emulsion,
at least one cosmetic active agent, in particular at least one deodorant active agent and/or antiperspirant active agent.

Cosmetic Composition

The term "antiperspirant active agent" means any substance which, by itself, has the effect of reducing or limiting the flow of sweat.

The term "deodorant active agent" means any substance that is capable of masking, absorbing, improving and/or reducing the unpleasant odor resulting from the decomposition of human sweat by bacteria.

The term "cosmetically acceptable" means compatible with the skin and/or its integuments, which has a pleasant color, odor and feel and which does not give rise to any unacceptable discomfort liable to put the consumer off using this composition.

Deodorant Active Agents

The cosmetic compositions according to the invention may contain one or more deodorant active agents, for instance:

bacteriostatic agents or bactericidal agents such as 2,4,4'-trichloro-2'-hydroxydiphenyl ether (triclosan), 2,4-dichloro-2'-hydroxydiphenyl ether, 3',4',5'-trichlorosalicylanilide, 1-(3',4'-dichlorophenyl)-3-(4'-chlorophenyl)urea (triclocarban) or 3,7,11-trimethyldodeca-2,5,10-trienol (Farnesol); quaternary ammonium salts, for instance cetyltrimethylammonium salts, cetylpyridinium salts; chlorhexidine and salts; diglyceryl monocaprate, diglyceryl monolaurate or glyceryl monolaurate; polyhexamethylene biguanide salts;

zinc salts such as zinc salicylate, zinc phenolsulfonate, zinc pyrrolidonecarboxylate (more commonly known as zinc pidolate), zinc sulfate, zinc chloride, zinc lactate, zinc gluconate, zinc ricinoleate, zinc glycinate, zinc carbonate, zinc citrate, zinc chloride, zinc laurate, zinc oleate, zinc orthophosphate, zinc stearate, zinc tartrate, zinc lactate or zinc acetate, or mixtures thereof;

odor absorbers such as zeolites, cyclodextrins, metal oxide silicates such as those described in application US2005/063928; metal oxide particles modified with a transition metal, as described in applications US2005/084464 and US2005/084474, aluminosilicates such as those described in application EP1658863, chitosan-based particles such as those described in U.S. Pat. No. 6,916,465;

substances that block the enzymatic reactions responsible for the formation of odorous compounds, such as arylsulfatase, 5-lipoxygenase, aminocylase or β-glucuronidase inhibitors;

and mixtures thereof.

The deodorant active agents can be present in the composition according to the invention in a proportion of from 0.01 to 10% by weight and preferably in a proportion of from 0.1 to 5% by weight relative to the total weight of the composition.

Antiperspirant Active Agents

The antiperspirant active agents are preferably chosen from aluminium and/or zirconium salts; complexes of zirconium hydroxychloride and of aluminium hydroxychloride with an amino acid, such as those described in U.S. Pat. No. 3,792,068, commonly known as "ZAG complexes". Such complexes are generally known under the name ZAG (when the amino acid is glycine). ZAG complexes ordinarily have an Al/Zr quotient ranging from about 1.67 to 12.5 and a metal/Cl quotient ranging from about 0.73 to 1.93. Among these products, mention may be made of aluminium zirconium octachlorohydrex GLY, aluminium zirconium pentachlorohydrex GLY, aluminium zirconium tetrachlorohydrate GLY and aluminium zirconium trichlorohydrate GLY.

Among the aluminium salts that may be mentioned are aluminium chlorohydrate, aluminium chlorohydrex, aluminium chlorohydrex PEG, aluminium chlorohydrex PG, aluminium dichlorohydrate, aluminium dichlorohydrex PEG, aluminium dichlorohydrex PG, aluminium sesquichlorohydrate, aluminium sesquichlorohydrex PEG, aluminium sesquichlorohydrex PG, alum salts, aluminium sulfate, aluminium zirconium octachlorohydrate, aluminium zirconium pentachlorohydrate, aluminium zirconium tetrachlorohydrate, aluminium zirconium trichlorohydrate and more particularly the aluminium hydroxychloride sold by the company Reheis under the name Reach 301 or by the company Guilini Chemie under the name Aloxicoll PF 40. Aluminium zirconium salts are, for example, the salt sold by the company Reheis under the name Reach AZP-908-SUF.

Aluminium chlorohydrate in activated or inactivated form will be used more particularly.

The antiperspirant active agents may be present in the composition according to the invention in a proportion of from 0.001 to 30% by weight and preferably in a proportion of from 0.5 to 25% by weight relative to the total weight of the composition.

The composition according to the invention preferably has a pH ranging from 3 to 9, depending on the support chosen.

Emulsion

The emulsion may in particular be a water-in-oil or oil-in-water emulsion, or a multiple emulsion (oil-in-water-in-oil or water-in-oil-in-water triple emulsion (such emulsions are known and described, for example, by C. Fox in "Cosmetics and Toiletries"—November 1986—Vol. 101— pages 101-112)).

i) Aqueous Phase

The aqueous phase of said compositions contains water and generally further water-soluble or water-miscible solvents. The water-soluble or water-miscible solvents comprise short chain, for example $C_1$-$C_4$, monoalcohols, such as ethanol or isopropanol; diols or polyols, for instance ethylene glycol, 1,2-propylene glycol, 1,3-butylene glycol, hexylene glycol, diethylene glycol, dipropylene glycol, 2-ethoxyethanol, diethylene glycol monomethyl ether, triethylene glycol monomethyl ether and sorbitol. Propylene glycol and glycerol will be used more particularly.

ii) Oily Phase

The oily phase may contain one or more volatile or non-volatile silicone oils, hydrocarbon-based oils or fluoro oils.

Volatile silicones are defined, in a known manner, as compounds that are volatile at room temperature. Among these compounds, cyclic and linear volatile silicones of the dimethylsiloxane type, the chains of which comprise from 3 to 9 silicone residues, may be mentioned. Preferably, cyclomethicones D4, D5 or D6 are chosen.

The additional volatile hydrocarbon-based oils can be chosen in particular from branched $C_8$-$C_{16}$ alkanes such as $C_8$-$C_{16}$ isoalkanes (also known as isoparaffins), isododecane, isodecane, isohexadecane and for example the oils sold under the trade name Isopar or Permethyl, branched $C_8$-$C_{16}$ esters such as isohexyl neopentanoate and mixtures thereof; isododecane is preferably used.

Non-volatile silicones are defined, in a known manner, as compounds with a low vapor pressure at room temperature. These compounds include: polyalkylsiloxanes, in particular linear polyalkylsiloxanes, for instance polydimethylsiloxanes, or linear dimethicones sold by the company Dow Corning under the name "Dow Corning 245 Fluid"; cyclopolydimethylsiloxanes (cyclomethicones); polydimethylsiloxanes comprising alkyl, alkoxy or phenyl groups, which are pendant or at the end of a silicone chain, these groups containing from 2 to 24 carbon atoms; phenyl silicones such as phenyl trimethicones, phenyl dimethicones, phenyltrimethylsiloxydiphenylsiloxanes, diphenyl dimethicones, diphenylmethyldiphenyltrisiloxanes, 2-phenylethyl trimethylsiloxy silicates, and polymethylphenylsiloxanes.

The non-volatile fluoro oils may be chosen from partially hydrocarbon-based and/or silicone-based fluoro oils, such as those described in document JP-A-2-295912.

The non-volatile hydrocarbon-based oils can be of mineral, synthetic or animal origin. They can be chosen from liquid paraffins, such as petrolatum, liquid petrolatum, perhydrosqualene, polydecenes, isohexadecane, isododecane or hydrogenated polyisobutene (or hydrogenated isoparaffin), such as Parleam oil; or fatty esters, preferably those obtained from an alcohol comprising a linear or branched chain having from 1 to 17 carbon atoms and from a fatty acid comprising a linear or branched chain having from 3 to 18 and preferably from 12 to 17 carbon atoms. Advantageously, said ester is a saturated ester which does not include either an ether group or a hydroxyl group (the total amount of carbon atoms in the ester can vary from 12 to 50 and preferably from 20 to 50).

As fatty esters, mention may be made, for example, of 2-ethylhexyl caprate/caprylate (or octyl caprate/caprylate), ethyl laurate, butyl laurate, hexyl laurate, isohexyl laurate, isopropyl laurate, methyl myristate, ethyl myristate, butyl myristate, isobutyl myristate, isopropyl myristate, 2-octyldodecyl myristate, 2-ethylhexyl monococoate (or octyl monococoate), methyl palmitate, ethyl palmitate, isopropyl palmitate, isobutyl palmitate, 2-ethylhexyl palmitate (or octyl palmitate), butyl stearate, isopropyl stearate, isobutyl stearate, isocetyl stearate, isostearyl isostearate, isopropyl isostearate, 2-ethylhexyl stearate (or octyl stearate), 2-ethylhexyl pelargonate (or octyl pelargonate), 2-ethylhexyl hydroxystearate (or octyl hydroxystearate), decyl oleate, diisopropyl adipate, di(2-ethylhexyl) adipate (or dioctyl adipate), diisocetyl adipate, 2-ethylhexyl succinate (or octyl succinate), diisopropyl sebacate, 2-ethylhexyl malate (or octyl malate), pentaerythritol caprate/caprylate, pentaerythritol tetraisostearate, 2-ethylhexyl hexanoate (or octyl hexanoate), octyldodecyl octanoate, isodecyl neopentanoate, isostearyl neopentanoate, cetearyl isononanoate, isodecyl isononanoate, isononyl isononanoate, isotridecyl isononanoate, lauryl lactate, myristyl lactate, cetyl lactate, myristyl propionate, 2-ethylhexyl 2-ethylhexanoate (or octyl 2-ethylhexanoate), 2-ethylhexyl octanoate (or octyl octanoate), and their mixtures, C12-C15 fatty alcohol benzoates (Finsolv T N from Finetex); isopropyl lauroylsarcosinate (Eldew S L 205 from Unipex) or dicaprylyl carbonate (Cetiol CC from Cognis).

The non-volatile hydrocarbon-based oils can also be dialkyl ethers, such as dicaprylyl ether (Cetiol OE from Cognis).

The non-volatile hydrocarbon-based oils can be oils of vegetable origin, such as, for example, sweet almond oil, avocado oil, castor oil, coriander oil, olive oil, jojoba oil, sesame oil, groundnut oil, grape seed oil, rapeseed oil, coconut oil, hazelnut oil, shea butter, palm oil, apricot kernel oil, calophyllum oil, rice bran oil, maize oil, wheat germ oil, soybean oil, sunflower oil, evening primrose oil, safflower oil, passionflower oil, rye oil or triglycerides of caprylic/capric acids, such as those sold by Stéarineries Dubois or those sold under the names Miglyol 810, 812 and 818 by Dynamit Nobel.

The non-volatile hydrocarbon-based oils can also be chosen from fatty acids, fatty alcohols, such as lauryl, cetyl, myristyl, stearyl, palmityl or oleyl alcohol, and 2-octyldodecanol.

Preferably, the cosmetic composition is free of solid particles and fillers.

More advantageously, the composition is free of perlite.

Propellant

The propellants are advantageously chosen from dimethyl ether (DME), volatile hydrocarbons such as n-butane, propane, isobutane, and mixtures thereof, optionally with at least one chlorinated and/or fluorinated hydrocarbon. Among the latter, mention may be made of the compounds sold by the company DuPont de Nemours under the names Freon® and Dymel®, and in particular monofluorotrichloromethane, difluorodichloromethane, tetrafluorodichloroethane and 1,1-difluoroethane, sold especially under the trade name Dymel 152 A by the company DuPont. Carbon dioxide, nitrous oxide, nitrogen or compressed air may also be used as propellant.

The composition containing the deodorant active agent(s) and the propellant(s) may be in the same compartment or in different compartments in the container.

According to the invention, the concentration of propellant preferably ranges between 50% and 95% by weight relative to the total weight of the pressurized composition. More preferably, the concentration of propellant ranges from 70% to 85% by weight relative to the total weight of the pressurized composition.

The term "pressurized composition" is understood to mean the total fluid+gas composition contained in the container.

Additives

The composition may also comprise: diols or polyols, such as ethylene glycol, 1,2-propylene glycol, 1,3-butylene glycol, hexylene glycol, diethylene glycol, dipropylene glycol, 2-ethoxyethanol, diethylene glycol monomethyl ether, triethylene glycol monomethyl ether, and sorbitol. Propylene glycol and glycerol will be used more particularly.

The cosmetic compositions according to the invention may also comprise cosmetic adjuvants chosen from waxes, softeners, antioxidants, opacifiers, stabilizers, moisturizers, vitamins, fragrances, bactericides, preserving agents, polymers, thickeners or any other ingredient usually used in cosmetics for this type of application.

Needless to say, a person skilled in the art will take care to choose this or these optional additional compounds such that the advantageous properties intrinsically associated with the cosmetic composition according to the invention are not, or are not substantially, adversely affected by the envisaged addition(s).

Device

In particular, the dispensing orifice is preferably defined between the body and the engaging part but may, alternatively, be defined entirely by the engaging part.

By virtue of the invention, a passage is formed through the dispensing head and more particularly through the body and the engaging part, allowing a flow of air to be established through the head when the product to be dispensed is emitted, and this can prove advantageous when the product is emitted in the form of a spray, allowing a current of air to be created through the head in order to accompany the flow of the spray.

In addition, the dispensing head has an appearance which contrasts clearly with the usual aesthetics of known dispensing heads, and which proves to be particularly attractive to the consumer.

Furthermore, the passage through the head can be produced with dimensions sufficient to allow, if desired, a finger or a lock of hair to be inserted into this passage. This can make it easier to apply a product to the finger or the lock of hair.

If desired, the invention can also make it easier to produce a dispensing orifice having an annular section between the engaging part and the body, allowing the formation of a hollow spray. Alternatively, a plurality of dispensing orifices are formed between the body and the engaging part, for example in order to dispense the product in the form of a number of sprays or jets. The number of dispensing orifices may in particular be greater than or equal to 10, better still greater than or equal to 20, even better still greater than or equal to 30. The dispensing orifices each exhibit for example a cross section greater than or equal to 0.003 $mm^2$, better still greater than or equal to 0.006 $mm^2$ and are preferably spaced apart from one another (measurement along a straight line between the centres of mass of the orifices) by a distance of more than 1 mm.

In another variant, several dispensing orifices are formed entirely in the engaging part. The orifices may be constructed in such a way that the jet exiting from each orifice swirls, especially by virtue of at least two swirl ducts oriented tangentially around the axis of the orifice. The engaging part may have a U-shaped axial half-section. The body may have two concentric mounting skirts between which the engaging part is fastened. The body may comprise a crown into which the engaging part is inserted, the crown possibly bearing one or more reliefs defining, with the engaging part, ducts, especially swirl ducts, for supplying the dispensing orifice.

The body may define a housing that receives the engaging part, which is then called a core.

The dispensing orifice(s) may be open at rest. The expression "at rest" should be understood as meaning before the engaging part is exposed to the pressure of the product to be dispensed. Thus, in this case, the dispensing orifice(s) are already formed and open when the product is sent into the head in order to be dispensed. Alternatively, the dispensing orifice is formed at the time the product is dispensed, by virtue for example of the elasticity of at least a portion of the body or of the engaging part, which deforms under the pressure of the product at the time it is dispensed.

By virtue of the invention, in the case of spraying, the spray can be emitted at a relatively high flow rate, if desired, while having a spray head which has a relatively simple design and functions reliably. In particular, the dispensing orifice may be produced with well-defined dimensions. In addition, the dispensing head may be aesthetically pleasing to the consumer.

The body may have a first surface that flares towards the outside, or converges towards the outside, and the engaging part may have a second surface, opposite the first surface, that diverges towards the outside, or converges towards the outside. The first surface may be conical. The second surface may be conical, with the same angle as the first surface or with a greater or smaller angle.

A different angle that results in a narrowing of the space may lead to an acceleration of the jet before it exits, and this may be advantageous in the context of a spray.

There may be one or more than one dispensing orifice and it may have an annular shape or some other shape. The dispensing orifice may have a constant width in the circumferential direction. The one or more dispensing orifices may be defined between two concentric surfaces of revolution, for example in the form of cylinders of revolution.

The dispensing orifice(s) may exhibit axial symmetry, preferably rotational symmetry, in particular around the dispensing axis. The dispensing axis is defined by the general direction in which the product is dispensed by the head.

The engaging part is preferably attached, thereby making it, and the body, easier to manufacture. Alternatively, the engaging part is molded in one piece with the body, in particular in the case of the dispensing of a foam, it then being possible for the dispensing orifice to have a larger section than in the case of the spraying of a spray.

The space formed between the body and the engaging part is supplied by at least one supply duct, the section of which is preferably greater than that of the dispensing orifice, thereby making it easier to fill this space before the product emerges through the dispensing orifice.

A product distribution chamber may advantageously be formed, between the engaging part and the body, upstream of the dispensing orifice. This can make the emission of a homogeneous spray, in particular, easier.

The supply duct for the product may open into this chamber, which preferably has an annular shape. Its width, which corresponds to the gap between the engaging part and the body, is preferably greater than the maximum width of the passage, via which the distribution chamber communicates with the dispensing orifice.

At least one of the body and the engaging part, preferably the body, may have at least one relief for centering the engaging part in relation to the body, and preferably at least ten, better still at least twenty, and even better still at least forty reliefs. These reliefs may extend as far as the edge of the part in which they are produced so as to generate a multitude of orifices via which jets of product exit, the centering reliefs being oriented in particular parallel to the dispensing axis or obliquely in the same circumferential direction around the axis, and optionally also being able to define, between one another, sectional narrowings that cause the jet of product to be accelerated. This or these reliefs are preferably located set back from the dispensing orifice when it is desired to generate a spray in the form of a single jet. The reliefs can be produced on the body, being for example in the form of axial ribs that are distributed regularly around the entire surface of the body opposite the engaging part.

The centering reliefs may optionally ensure alone that the engaging part is held on the body. Alternatively, the engaging part is fixed to the body somewhere other than in the region of the centering reliefs, it being possible in this case for the centering reliefs to have or not have a function of holding the engaging part on the body.

Preferably, the engaging part is fixed in relation to the body. Alternatively, the engaging part is fixed in an adjustable manner in relation to the body, in order for example to allow the user to adjust the width of the dispensing orifice or to close the latter when not in use, for example by screwing it through a quarter turn, this screwing being accompanied by an axial movement of the engaging part in relation to the body.

The engaging part may be flush with the front end of the body so as to generate a spray with an axis substantially parallel to the axis of the engaging part.

The engaging part may extend axially beyond the front end of the body by an amount between 0 and 1 mm, better still between 0 and 0.5 mm. The spray may then diverge away from the axis of the engaging part.

The engaging part may be axially set back from the front end of the body by an amount between 0 and 1 mm, better still between 0 and 0.5 mm. The spray may then converge towards the axis of the engaging part.

The invention makes it possible to easily produce, if desired, a dispensing orifice having a circular internal contour. The inside diameter of the passage formed through the head is for example greater than or equal to 10 mm, better still greater than or equal to 15 mm, 20 mm or 30 mm. When the passage does not have a circular section, the "inside diameter" denotes the diameter of the largest circle inscribed in this passage.

The head may have at least two housings and two engaging parts that are disposed in the housings and each define with the body, at rest, a dispensing orifice according to the invention. The dispensing axes may then be parallel or not parallel, intersecting or not intersecting, for example converging towards one another.

The dispensing orifice may have, in axial half-section, an axis that converges or diverges in relation to the spraying direction.

A further subject of the invention, according to another of its aspects, is a container provided with a dispensing head according to the invention.

Advantageously, the dispensing orifice has a triangular cross section.

More advantageously, the engaging part at least partially defines a plurality of dispensing orifices, the individual cross sections of the dispensing orifices being between 0.01 mm$^2$ and 0.5 mm$^2$.

Even more advantageously, the number of dispensing orifices is greater than or equal to 5, preferably greater than or equal to 10.

Preferably, the individual cross sections of the dispensing orifices are between 0.03 mm$^2$ and 0.4 mm$^2$, and preferably between 0.05 mm$^2$ and 0.4 mm$^2$.

The invention also relates to a device for dispensing a cosmetic composition, said device comprising a dispensing head intended to be fitted on a container containing said cosmetic composition to be dispensed,
 the dispensing head comprising:
  a body (3),
  an engaging part (10), in particular a core (10), defining with the body (3), at rest, a dispensing orifice (12) having in particular an annular section,
 the cosmetic composition comprising, in a cosmetically acceptable medium,
 at least one emulsion chosen from a water-in-oil emulsion and an oil-in-water emulsion,
 at least one cosmetic active agent, in particular at least one deodorant active agent and/or antiperspirant active agent.

The invention also relates to a device for dispensing a cosmetic composition, said device comprising a dispensing head intended to be fitted on a container comprising a valve rod or pump rod, the dispensing head comprising:
- a body provided with an end piece for connecting to the valve rod or pump rod,
- a part attached to the body, at least partially defining a dispensing orifice having in particular an annular section at rest or several dispensing orifices distributed around a dispensing axis (Z), the head not being a through-head along the dispensing axis (Z), a) the body being closed along the dispensing axis (Z) and said part being in particular of annular shape, or b) the body having a through-opening along the dispensing axis (Z) and said part closing this opening, the cosmetic composition comprising, in a cosmetically acceptable medium, at least one emulsion chosen from a water-in-oil emulsion and an oil-in-water emulsion, at least one cosmetic active agent, in particular at least one deodorant active agent and/or antiperspirant active agent.

Features of the orifices:

Their individual cross sections are advantageously a disc.

They are ideally cylindrical in shape for ease of use, or approximately cylindrical in shape.

The depth of the orifice is advantageously between 0.5 and 2 mm, a great length makes it possible to create an individual spray with a small cone so as to create a tubular effect with a large number of orifices, a small length allows a very wide individual spray and expands even further the area of application of the multi-orifice diffuser.

The type of valve selected is advantageously provided with a nozzle comprising one 0.5 mm orifice with an internal restriction of 0.8 mm and an additional gas intake of 0.4 mm.

The sum of the cross sections of the orifices in the ring has been chosen to be close to the area of the orifice in the nozzle. For example, for an orifice having a diameter of 0.5 mm, a section of 0.196 mm$^2$ is chosen. Very small orifice sections are obtained for 40 holes (around 0.005 mm$^2$) and for 20 holes (around 0.01 mm$^2$).

With an unchanged valve, several options are available for producing the device in accordance with the type of spraying desired.

gentle mist: 80 orifices of 0.005 mm$^2$
small flow rate: 20 orifices of 0.005 mm$^2$
powerful effect: 20 orifices of 0.01 mm$^2$
powerful effect: 40 orifices of 0.01 mm$^2$
very powerful effect: 40 or 80 orifices of 0.01 mm$^2$ with larger additional gas intake (diameter between 0.45 mm and 0.50 mm).

This makes it possible to envisage the range of possibilities both in terms of the number of orifices and in terms of the sections or strengths of the sprays. Similarly, the level of gas can be reevaluated depending on the needs.

Distribution of the orifices: These can be

Equidistant around the periphery of the ring

Mutually equidistant over a portion of the ring

Distributed in equidistant groups (e.g. X equidistant portions (around the periphery or over a portion of the ring) made up of several equidistant orifices).

It is possible to create a ring fully supporting the diffuser orifices which may be cylindrical. In this configuration, it is possible to produce mini swirl ducts with a different design from the internal and external rings so as to allow the creation of a ring intended to create the "center post" function at the rear.

The product may be a cosmetic product to be dispensed in the form of a spray or of a foam.

The container may be a pressurized container, provided for example with a hollow valve rod inserted into a housing in the head that is suitable for holding said rod.

The invention may be better understood from reading the following detailed description of non-limiting illustrative embodiments thereof and from examining the appended drawing, in which:

FIGS. 10A and 10B are front views along X of different examples of configurations according to FIG. 9.

In the drawing, the actual respective proportions of the various constituent elements have not always been respected, for the sake of clarity.

Figure 1:
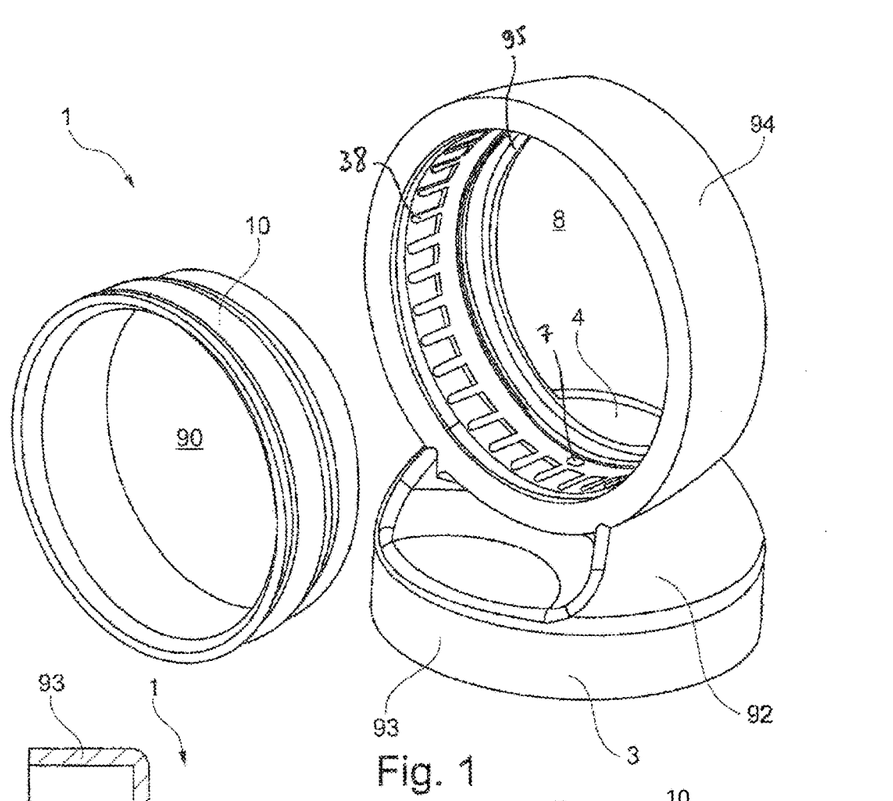
FIG. 1 schematically shows a perspective view of an example of a dispensing head produced in accordance with the invention, before the engaging part is fitted on the body of the head.
Figure 2:
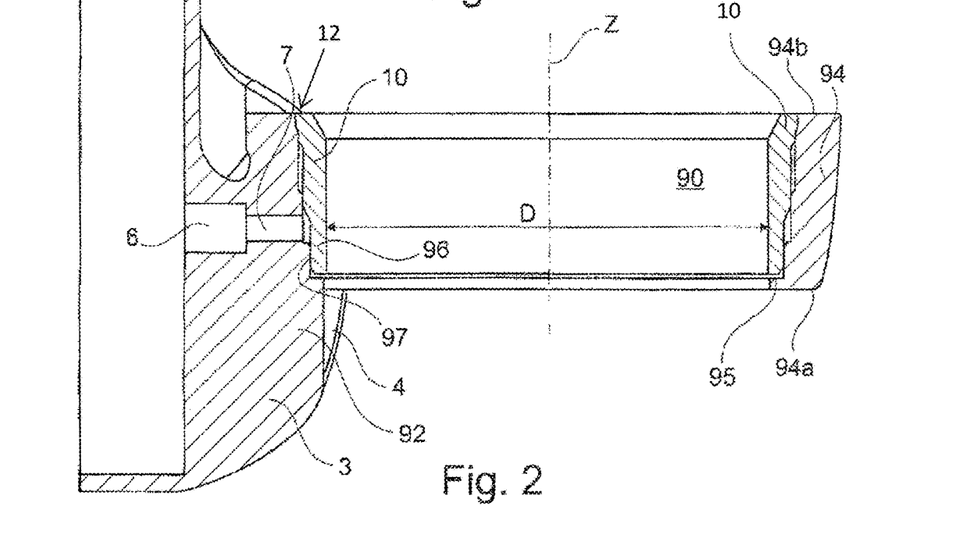
FIG. 2 shows the dispensing head after the engaging part has been fitted in the body.
Figure 3:
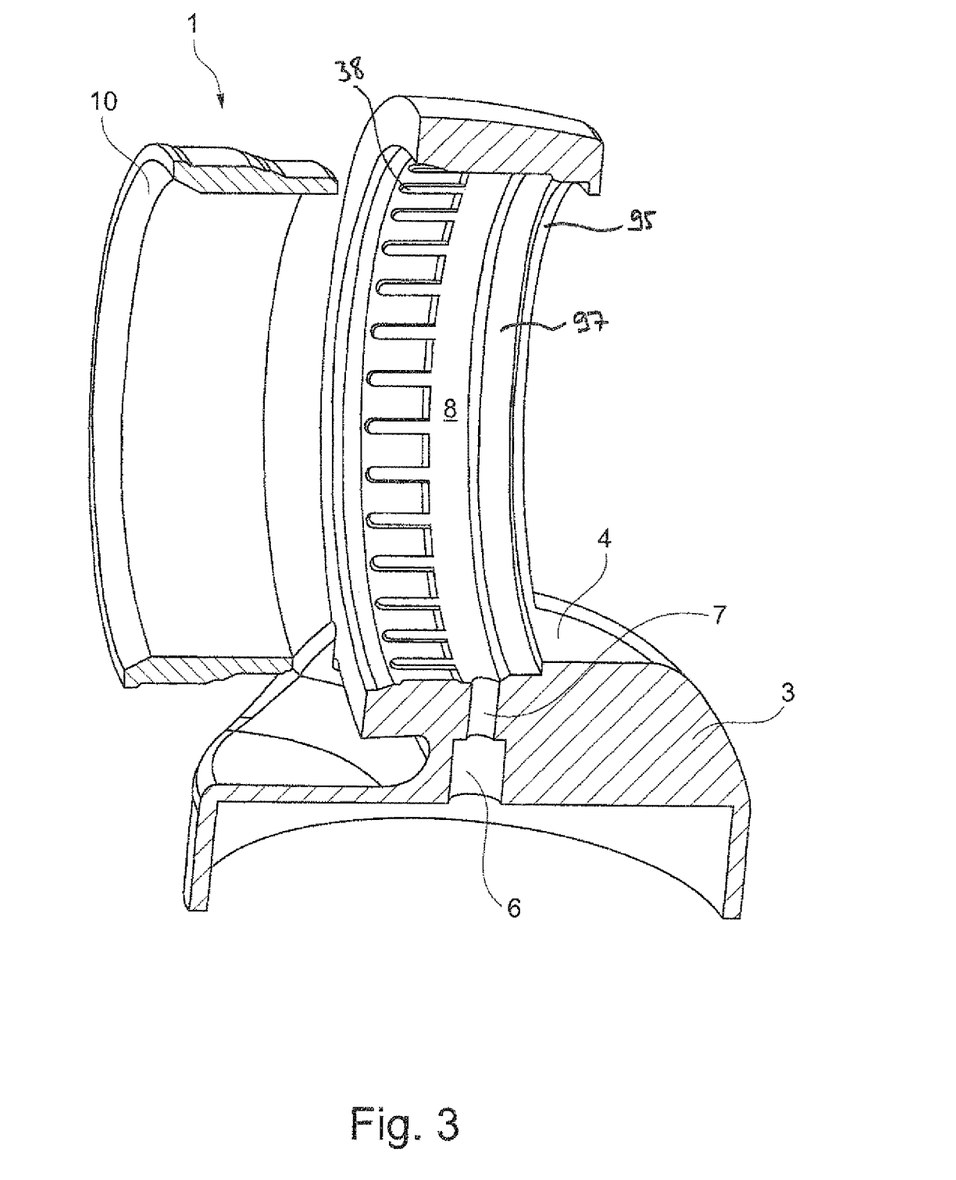
FIG. 3 is a view similar to FIG. 1 in partial section.

The dispensing head 1 shown in FIGS. 1 to 3 is intended to be fitted on a container (not shown) provided with a hollow valve rod or hollow pump rod, through which the product to be dispensed that is contained in the container is conveyed towards the head 1.

The container may in particular be a pressurized container of the aerosol can type, containing a propellant gas such as compressed air, for example, or a liquefied gas.

The container may be provided with a valve and the valve may be opened for example by pressing the hollow rod or alternatively by tilting the latter. When the container is provided with a pump, the pump may be actuated for example by pressing the hollow rod along its longitudinal axis.

The head 1 comprises a body 3 which may be produced in an integral manner by molding a single part or may comprise a plurality of elements produced separately and joined together.

The dispensing head 1 may comprise, as can be seen in FIG. 2, a housing 6 intended to engage with the hollow rod in order to allow the product delivered through the latter to reach a supply duct 7 which opens into a housing 8 in the body 3. The housing 6 has a size adapted to the outside diameter of the rod, so as to obtain a sealed fit of the rod in the housing 6, in order that the product delivered through the rod passes entirely into the supply duct 7. The latter is for example coaxial with the rod of the container but could be oriented in some other way and have for example a plurality of differently oriented portions.

An engaging part 10, called core in the following text when it is inside the body, is fixed in the housing 8 and defines for example with the body 3 a dispensing orifice 12 having an annular section, as illustrated.

The expression "annular section" should be understood within the meaning of the present invention as meaning any section that follows a closed contour, whether this contour is circular, elliptical, polygonal or some other shape.

Passing axially through the core 10 is an opening 90, the inside diameter D of which may be relatively large, for example greater than or equal to 10 mm, better still 15, 20 or 30 mm.

The opening 90 helps to give the head a particularly aesthetic appearance. In addition, the opening 90 can allow air to flow through the head under the entrainment effect of a spray emitted through the dispensing orifice 12. This can help to increase the range of the spray and can increase the freshness effect provided thereby, if need be.

The opening 90 may also allow a finger or a lock of hair to be inserted through the head, and this can make it possible to apply a product in a single movement over the entire circumference of the element inserted through the head. This can be an advantage for applying for example an antiseptic or care product to a finger or for treating a lock of hair.

The dispensing axis Z may be perpendicular to the longitudinal axis X of the container on which the head is fitted, as illustrated.

The head 1 comprises a base 92 which defines a surface 4 which the user can press in order to bring about dispensing.

The bottom of the base 92 can be extended by an enclosing skirt 93 which covers the upper part of the container.

The housing 8 which receives the core 10 is defined by a crown 94 of axis Z, the lower side of which is joined to the base 92. The supply duct 7 passes through the base 92 and leads into the housing 8 at a distance from the axial ends, along the axis Z, of the crown 94, being preferably closer to the rear end 94a than to the front end 94b, as can be seen in FIG. 2.

The body 3 may have, as illustrated, a shoulder 95 close to the rear end 94a, against which the core 10 can come into axial abutment, if need be, at the end of its fitting.

The core 10 and the housing 8 may have annular surfaces 96 and 97, in sealed contact, in order to close the space formed between the core 10 and the body 3 at the rear of the supply duct 7.

Preferably, the circumferential width/of the dispensing orifice 12, around the spraying direction Z, is constant. If this width/varies, for example so as to take into account the possibly non-uniform pressure drop experienced by the flow of product upstream of the dispensing orifice 12, this does not depart from the scope of the present invention. This non-uniform pressure drop results for example from the geometry of the space between the core and the body, in particular the presence of angles or intersections. By varying the width 1, it is possible to ensure that the product can emerge more easily at the point where this pressure drop is greatest, if a spray which is as homogeneous as possible is desired.

The width/of the dispensing orifice is for example between 0.01 and 2 mm.

The core 10 can be fixed to the body 3 in various ways. In the example illustrated in FIGS. 1 to 3, the core 10 is retained on the body 3 by friction.

In the example illustrated, the core 10 is produced separately from the body 3 and is attached to the latter. The core 10 can be produced from the same thermoplastic material as the body 3 or alternatively from a different thermoplastic material. It is also possible to use a metal material to produce the core 10.

Figures 12A, 12B, 12C:
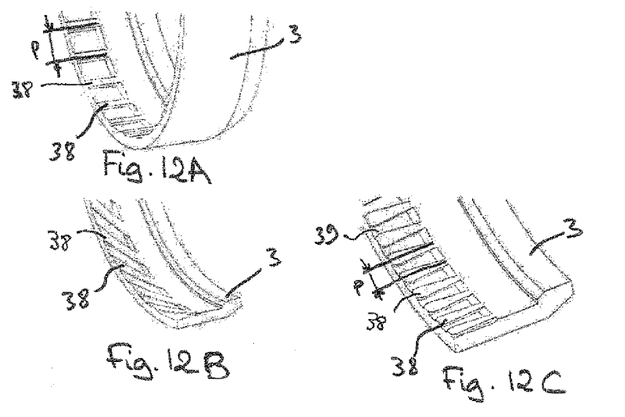
FIGS. 12A to 12C illustrate various examples of arrangements of the reliefs on the body.

Axial ribs 38 are formed on the internal circumference of the housing 8, as can be seen in particular in FIGS. 1 and 3, in order to center the core 10 in the housing 8. The centering reliefs 38 may be, as illustrated in FIGS. 12A to 12C, parallel or oblique in the circumferential direction with respect to the axis Z, or curved. Each relief 38 may have, when seen in a top view, a contour that is polygonal, in particular rectangular or trapezoidal, or that has a shape that is flared in the direction of the dispensing edge. Two centering reliefs 38 may define, between one another, a narrowing 39 in the vicinity of the dispensing orifice so as to accelerate the fluid via the Venturi effect. The number of centering reliefs 38 is preferably at least 10, better still 20, even better still 40.

Figures 4A, 4B, 4C, 5, 6, 7, 8A, 9, 10:
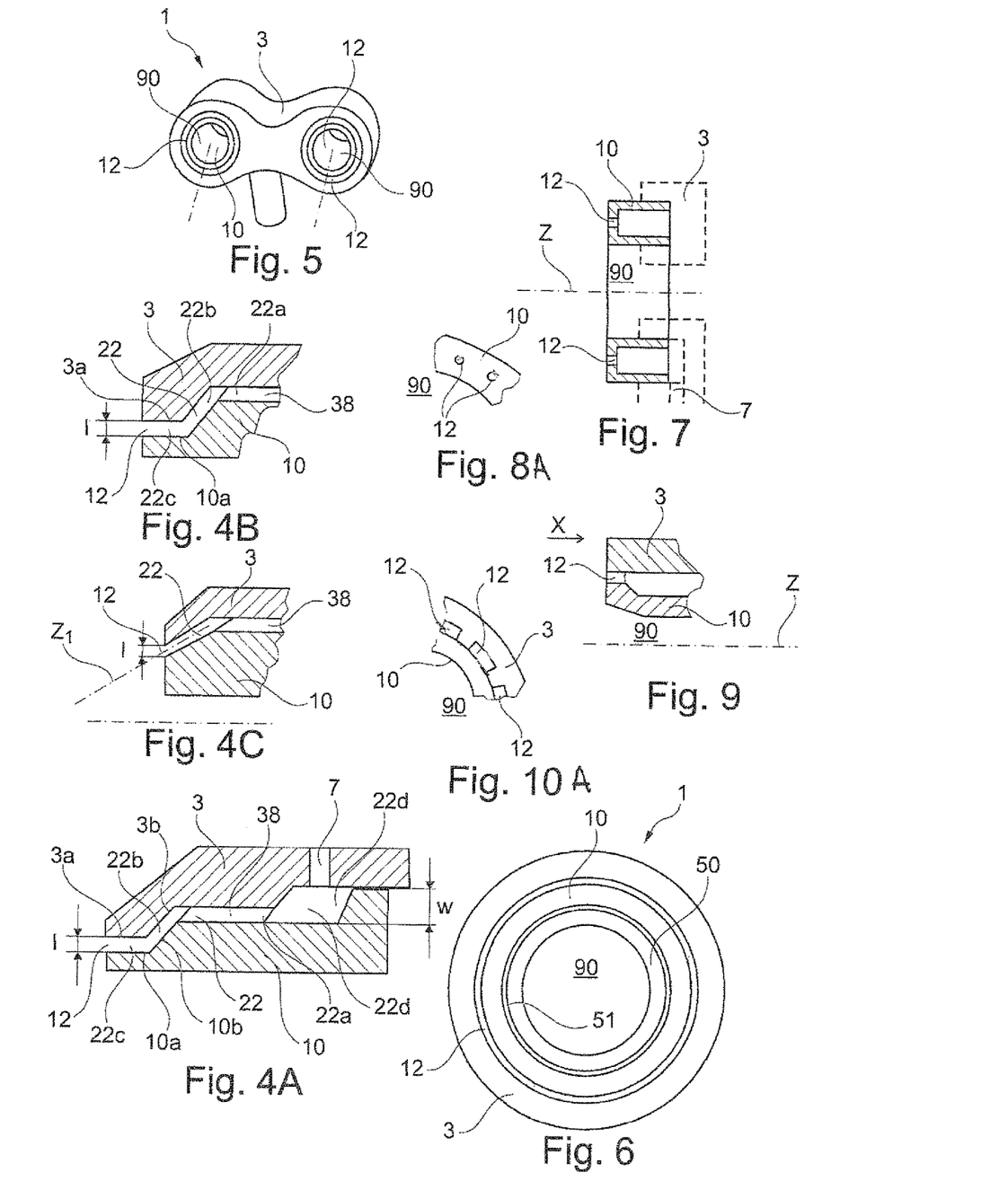
FIGS. 4A to 4F illustrate various arrangements, among others, of the engaging part and the body.
FIG. 5 illustrates the possibility of producing the dispensing head with two dispensing orifices according to the invention.
FIG. 6 shows a front view of a dispensing head having concentric dispensing orifices.
FIG. 7 is an axial section through a variant embodiment of the engaging part.
FIGS. 8A and 8B are partial front views of different examples of configurations of the engaging part from FIG. 7.
FIG. 9 is a partial axial section through a variant embodiment of the dispensing orifice.

The space 22 formed between the core 10 and the body 3 may have the configuration illustrated schematically in FIG. 4A, and open onto the dispensing orifice 12 by way of an annular terminal portion 22c formed between two surfaces 3a and 10a which are in the form of cylinders of revolution about the axis Z.

The terminal wall 22c is attached to a proximal portion 22a by way of an inclined intermediate portion 22b formed between opposite surfaces 3b and 10b.

The centering reliefs 38 extend in the proximal portion 22a. The latter is supplied with product via the distribution chamber 22d.

When the user actuates the dispensing head 1, the product passes through the supply duct 7 into the space 22 between the core 10 and the body 3 and can be delivered in the form of a spray through the dispensing orifice 12.

In the example in FIGS. 1 to 3, the spray is continuous angularly around the dispensing axis on account of the absence of contact between the core 10 and the body 3 in the region of the dispensing orifice 12. Specifically, the bearing region or regions between the core 10 and the body 3 are for example located, as illustrated, set back from the dispensing orifice 12 by a distance (measured along the dispensing axis Z) of at least 0.5 mm.

The spray may be discontinuous angularly around the dispensing axis on account of the presence, in particular at the reliefs 38, of contact between the core 10 and the body 3 where the product emerges.

Preferably, the cross section of the supply duct 7 is greater than the section of the dispensing orifice 12 so as to allow the space located upstream of the dispensing orifice to be filled rapidly with the product, this being able to help to form a homogeneous spray right from the start of spraying.

The distribution chamber 22d formed upstream of the space 22a in which the centering reliefs 38 extend receives the product delivered through the supply duct 7.

The width ω of the distribution chamber 22d is greater than that/of the terminal portion 22c which opens onto the dispensing orifice 12.

The distribution chamber 22d improves the distribution of the product before the latter reaches the narrower portions of the passage through which the product is evacuated.

FIGS. 4B and 4C illustrate different other examples of possible configurations for the space 22 formed between the core 10 and the body 3 for the product to flow to the dispensing orifice.

In the example in FIG. 4B, the space 22 formed between the core and the body comprises a proximal portion 22a in which the reliefs 38 for centering the core 10 in relation to the body 3 extend, extended by an intermediate portion 22b which forms an angle with the spraying direction Z, for example a re-entrant angle. This intermediate portion 22b can be attached to a terminal portion 22c, which opens onto the dispensing orifice 12, this terminal portion being defined for example, as illustrated, between two surfaces 3a and 10a, in the form of cylinders of revolution, parallel to the dispensing direction Z. The variant in FIG. 4B does not have a distribution chamber.

In the variant in FIG. 4C, the terminal portion 22c communicates directly with that portion 22a in which the centering reliefs 38 extend. The terminal portion 22c forms, for example, an angle with the dispensing direction Z. Thus, in axial half-section, the axis $Z_1$ of the orifice 12 is for example convergent, as illustrated.

Figure 4D:
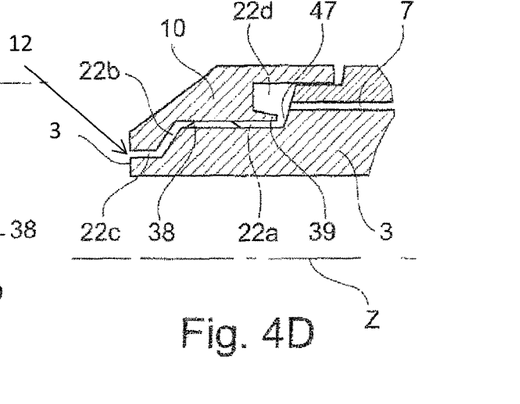

In the variant in FIG. 4D, the engaging part 10 is outside the body 3. The engaging part 10 is fixed to the body 3 so as to form with the latter the distribution chamber 22d, facing the supply duct 7. The portions 22a, 22b and 22c allow the product to be conveyed to the dispensing orifice 12.

The supply duct 7 opens for example into the distribution chamber 22d via a portion oriented parallel to the dispensing axis Z.

Centering reliefs 38 are produced for example on the body 3. The engaging part 10 can be produced, as illustrated, with an annular lip 39 which partially delimits the distribution chamber 22d and forms a narrowing 47 of the section between the chamber 22d and the portion 22a.

Figure 4E:
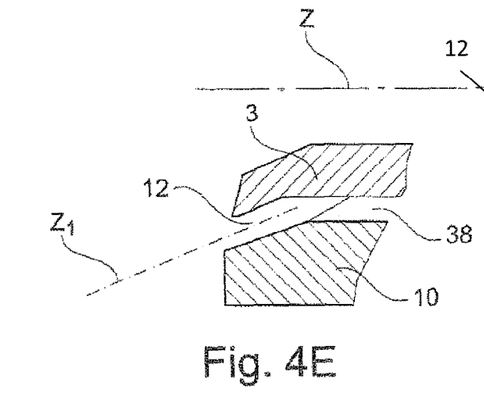

FIG. 4E illustrates the possibility of having an angle which is divergent between the axis $Z_2$, in axial half-section, of the orifice 12 and the dispensing axis.

Figure 4F:
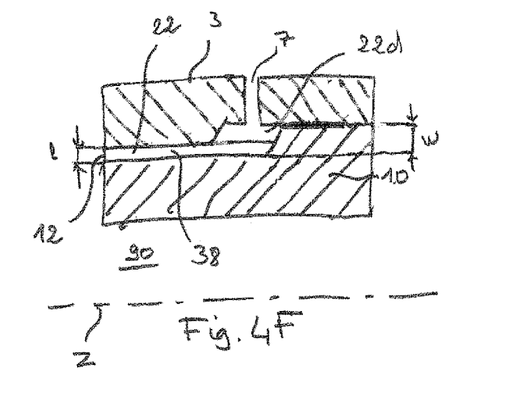

In the variant in FIG. 4F, the possibility of having no angle between the dispensing axis and the axis Z of the engaging part 10 is illustrated. The supply duct 7 opens for example onto a distribution chamber 22d. The product is conveyed towards the dispensing orifice 12 via ducts 22 comprising the reliefs 38. The reliefs 38 extend as far as the edge of the dispensing orifice 12 and define a plurality of orifices allowing the product to be delivered in the form of a plurality of jets.

The invention is not limited to a dispensing head comprising only one dispensing orifice 12 produced in accordance with the invention.

By way of example, FIG. 5 illustrates a dispensing head 1 which comprises two dispensing orifices 12.

When there are a plurality of dispensing orifices, these may be distributed in multiple ways on the dispensing head. For example, the spraying axes are parallel, or form an angle, in that, for example, they intersect.

Figure 8B:
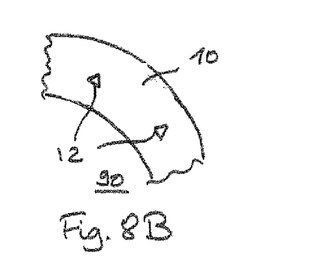

FIGS. 7, 8A and 8B illustrate the possibility for the dispensing head to have a plurality of dispensing orifices 12 formed entirely in the core 10 in order to dispense the product in the form of a plurality of jets for example. The dispensing orifices 12 may have many shapes when observed along their transverse axis, especially being circular or triangular, as illustrated in FIGS. 8A and 8B. The dispensing orifices 12 may be drilled into the core 10, for example by laser drilling.

The core 10 may have a U-shaped axial half-section, as illustrated in FIG. 7. The body 3 may comprise two concentric mounting skirts 41 which define between them a space for mounting the core 10, and may comprise, at its center, a crown 43 serving to support the engaging part 10. The skirts 41 define, with the crown 43, two annular ducts 45 into which the arms of the U fit. The crown 43 may have, for each orifice 12, two ducts 22 for supplying liquid to this orifice 12.

Figure 14:
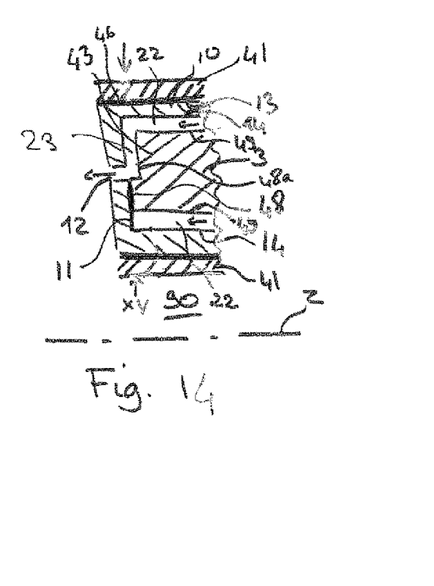
FIG. 14 is a partial axial section through a variant embodiment of the dispensing orifice.
Figure 15:
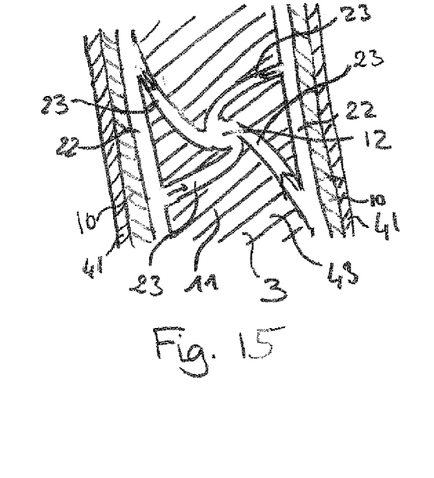
FIG. 15 is a section along XV in FIG. 14.
Figure 16:
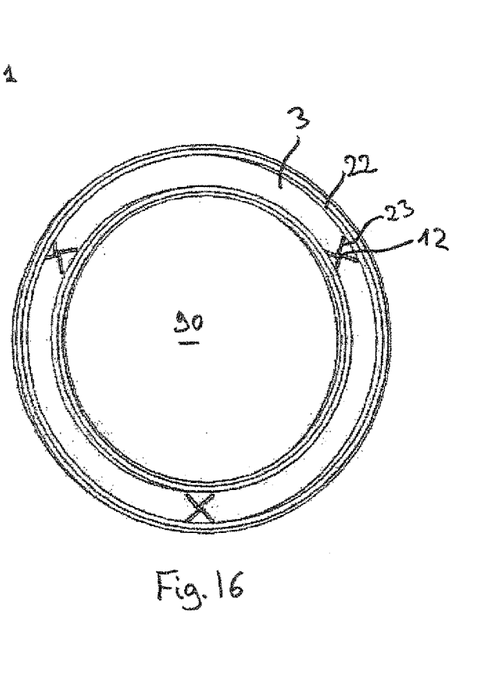
FIG. 16 is an exemplary embodiment of the body according to FIG. 14.
Figure 17:
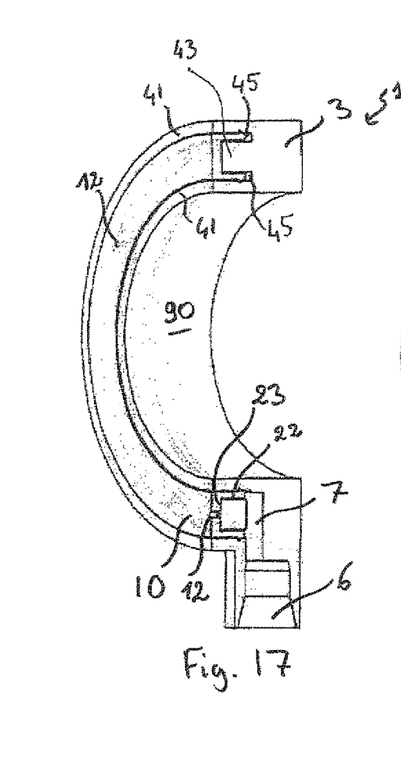
FIG. 17 is a cutaway perspective view of an example of a dispensing head according to the configuration in FIG. 14.

During mounting, as illustrated in FIGS. 14 and 17, the core 10 may bear against the protrusion 43, the end face 48 of the crown 43 being in contact with the internal face 11 of the core 10. The arms of the U of the core 10 are fixed in the ducts 45, the internal face 46 of the mounting skirts 41 being in contact with the face 13 of the core 10. The internal faces 14 of the arms of the U and the lateral surfaces 49 of the crown 43 may define, between one another, the ducts 22 for supplying liquid to the dispensing orifice 12. The crown 43 may have, especially in the form of impressions, on its outer face 48, supply ducts 23 allowing the liquid to pass from the supply ducts 22 to the dispensing orifice 12.

The supply ducts 22 open, upstream of the dispensing orifices 12, onto the supply ducts 23, which lead to the dispensing orifice 12. The supply ducts 23 generate, via their orientation relative to the dispensing orifice, a swirling flow at the outlet of the dispensing orifice 12. This configuration is more particularly useful in the case of a non-liquefied carrier gas.

In one variant, the supply ducts 22 may take the form of impressions on the lateral surface 49 of the body and/or on the internal faces 14 of the core 10.

In one variant (not shown), the core 10 possesses, especially in the form of impressions on its internal face 11, supply ducts 23, the end face 48 of the crown 43 being able to be smooth.

In one variant, the crown 43 is not circumferentially continuous and defines protrusions. The protrusions are placed upstream of the dispensing orifices 12 and may possess, upstream of the dispensing orifices 12, supply ducts 22 and 23 such as described above.

Figure 10B:
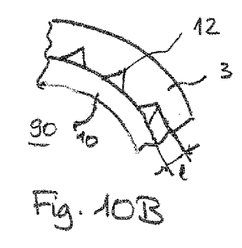

In the variant in FIGS. 4F, 9 and 10, the dispensing orifices 12 are formed between the core 10 and the body 3, being for example distributed all around the spraying axis Z. The core 10 or the body 3 may have centering reliefs 38 that circumferentially bound the dispensing orifices 12. The centering reliefs 38 may, as illustrated in FIGS. 12A to 12C, extend as far as the edge of the core 10 over its entire periphery and define, between one another, dispensing orifices 12. The number of dispensing orifices 12 is preferably at least 10, better still 20, even better still 40. The individual cross section of a dispensing orifice 12 is for example greater than 0.003 mm². The dispensing orifices 12 are preferably spaced apart by a space of at least 1 mm, which is the same as the pitch p between the centering reliefs. As illustrated in FIGS. 10A and 10B, the dispensing orifices 12 can have a polygonal cross section, in particular a triangular cross section.

Figures 13A, 13B, 13C:
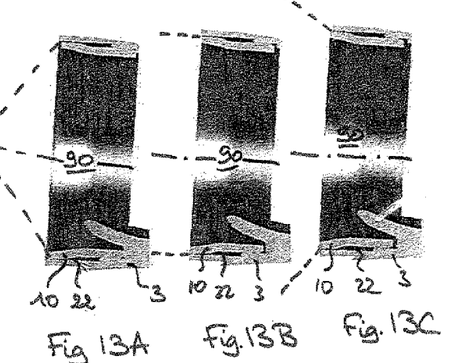
FIGS. 13A to 13C illustrate various examples of configurations of the engaging part with respect to the body.

The core 10 may, as illustrated in FIG. 13A, extend set-back relative to the body by an amount between 0 and 1 mm, better still between 0 and 0.5 mm. The body 3 protrudes into the dispensing orifice and may generate a convergent spray.

The core 10 may, as illustrated in FIG. 13B, be flush with the body 3. The spray can then be straight.

The core 10 may extend, as illustrated in FIG. 13C, forwards relative to the body 3 by an amount between 0 and 1 mm, better still between 0 and 0.5 mm. The spray can then be divergent.

If an additional dispensing orifice is provided, for example by attaching inside the core 10 a second core 50 which defines with the first core 10 a second dispensing orifice 51 which is coaxial with the first dispensing orifice, as illustrated in FIG. 6, this does not depart from the scope of the present invention. A passage 90 continues to be formed through the dispensing head.

The dispensing orifice may be supplied with more than one product.

The dispensing head may be supplied with two products which are dispensed through separate dispensing orifices.

Figure 11:
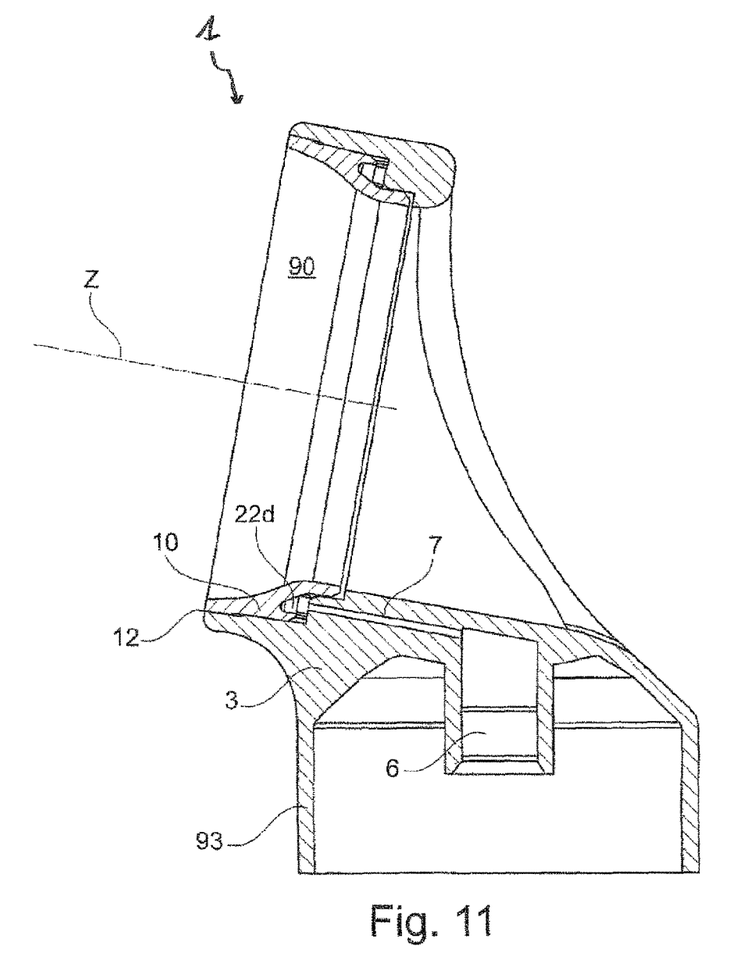
FIG. 11 is a view similar to FIG. 2 of a variant embodiment of the head.

It is possible for the axis Z not to be perpendicular to the axis of the rod of the container on which the head is fitted, as illustrated in FIG. 11. In this example, the axis Z is oriented upwards when the container is vertical with the dispensing head at the top.

The supply duct 7 can be oriented substantially parallel to the dispensing axis Z, at least in the case of the portion which opens out next to the engaging part 10. The latter may be produced with an annular lip 39 which defines a narrowing of the section 47.

The configuration may be similar to that in FIG. 4D apart from the fact that the engaging part 10 is outside the body 3 in the example in FIG. 4D and inside it in the example in FIG. 11.

The dispensing head may be arranged so as to allow a protective cap to be fitted and to comprise, if need be, an on/off system that makes it possible to prevent the actuation of the device when the dispensing head is in a certain position with respect to the container or when a locking element of the dispensing head is in a certain position in relation to the latter.

In variants which are not illustrated, the dispensing orifice is formed between a body and an engaging part, the body being radially on the inside with respect to the engaging part, the supply duct for the product passing through the body. All of the features described with reference to the figures can be found in variants in which the body is radially on the inside with respect to the engaging part.

The expression "comprising a" should be understood as being synonymous with "comprising at least one".

EXAMPLE i) Device

Three devices fitted with a dispensing head shown in FIG. 1 are prepared. The following are varied:

the number of holes and the section of the holes in the dispensing head, and the chemical compositions contained in these devices.

ii) Chemical Composition

The following commercial compositions are evaluated:

Device 1: Women's Aerosol AT GARNIER Mineral Invisible Black White Colors®

Device 2: Women's Aerosol AT GARNIER Mineral Invisible Black White Colors® perlite free iii) Evaluation of the Devices a) Evaluation of the quality of the spray

| Device number | No. of holes | Section of holes | Spraying without blockage |
|---|---|---|---|
| Device 1 | 10 | 0.027 | ++++++++++++ |
| Device 1 | 20 | 0.0121 | − |
| Device 2 | 10 | 0.027 | ++++++++++++ |
| Device 2 | 20 | 0.0121 | ++++++++++++ |

++++++++++++: very good spraying
−: blockage b) Conclusion from the Above Table

Device 2 results in better quality of spraying than device 1. The presence of perlite reduces the quality of spraying.

For device 1 and device 2, very good spraying is obtained with 10 holes, with or without perlite in the composition.

The invention claimed is:

1. A device for dispensing a cosmetic composition, the device comprising a dispensing head comprising:
   a base fitted on a container containing the cosmetic composition;
   an annular housing disposed on the base and comprising a supply duct configured to guide the cosmetic composition from the container to an inner surface of the housing;
   an annular core disposed inside the housing and having an inner surface that defines an opening of the dispensing head; and
   axial ribs disposed between the core and the housing, the ribs at least partially defining dispensing orifices configured to divide the cosmetic composition into separate streams and dispense the separate streams from the dispensing head, such that the streams are oriented parallel to a dispensing axis that extends axially through the annular core or converge upon the dispensing axis outside of the opening of the dispensing head,
   wherein the individual cross section of each dispensing orifice ranges from 0.01 mm$^2$ to 0.5 mm$^2$, and
   wherein the cosmetic composition comprises:
     at least one emulsion chosen from a water-in-oil emulsion and an oil-in-water emulsion; and
     at least one cosmetic active agent.

2. The device of claim 1, wherein each dispensing orifice is annular and has a constant width in the circumferential direction.

3. The device of claim 1, wherein each dispensing orifice exhibits axial symmetry.

4. The device of claim 1, wherein each dispensing orifice has a triangular cross section.

5. The device of claim 1, wherein the dispensing orifices vary in size, such that the dispensing orifices are configured to accelerate the streams of the cosmetic composition.

6. The device of claim 5, wherein the number of dispensing orifices is greater than or equal to 5.

7. The device of claim 5, wherein the individual cross sections of the dispensing orifices range from 0.03 mm$^2$ to 0.4 mm$^2$.

8. The device of claim 1, wherein an oily phase of the emulsion comprises at least one hydrocarbon-based oil.

9. The device of claim 1, wherein an oily phase of the emulsion comprises at least one silicone oil.

10. The device of claim 1, wherein the cosmetic composition is free of solid particles and fillers.

11. The device of claim 1, wherein the cosmetic composition is free of perlite.

12. A process for the dispensing of a cosmetic composition comprising:

dispensing a cosmetic composition from a dispensing device, the device comprising a dispensing head comprising:

a base fitted on a container containing the cosmetic composition to be dispensed;

an annular housing disposed on the base and comprising a supply duct configured to guide the cosmetic composition from the container to an inner surface of the housing;

an annular core disposed inside the housing and having an inner surface that defines an opening of the dispensing head; and axial ribs disposed between the core and the housing, the ribs at least partially defining dispensing orifices configured to divide the cosmetic composition into separate streams and dispense the separate streams from the dispensing head, such that the streams are oriented parallel to a dispensing axis that extends axially through the annular core or converge upon the dispensing axis outside of the opening of the dispensing head, wherein the individual cross section of each dispensing orifice ranges from 0.01 $mm^2$ to 0.5 $mm^2$, and wherein the cosmetic composition comprises:

at least one emulsion chosen from a water-in-oil emulsion and an oil-in-water emulsion, and at least one cosmetic active agent.

* * * * *